United States Patent [19]

Wolfson

[11] 4,165,736
[45] Aug. 28, 1979

[54] APPARATUS FOR OCULAR PLETHYSMOGRAPHY

[75] Inventor: Sumner H. Wolfson, Tucson, Ariz.

[73] Assignee: Zira International, Tucson, Ariz.

[21] Appl. No.: 800,884

[22] Filed: May 26, 1977

[51] Int. Cl.² ............................................. A61B 5/02
[52] U.S. Cl. .................................................. 128/687
[58] Field of Search ..................... 128/2.05 E, 2.05 P, 128/2.05 Q, 2.05 R, 2.05 V, 2 T

[56] References Cited

U.S. PATENT DOCUMENTS

| | | | |
|---|---|---|---|
| 1,708,432 | 4/1929 | Sprigg | 128/346 |
| 1,756,670 | 4/1930 | Treat | 128/346 |
| 3,308,810 | 3/1967 | Galin | 128/2 T |
| 3,396,720 | 8/1968 | Ohkubo | 128/297 |
| 3,911,903 | 10/1975 | Gee et al. | 128/2 T |

Primary Examiner—William E. Kamm
Attorney, Agent, or Firm—J. Michael McClanahan

[57] ABSTRACT

Apparatus is described to measure the pulsatile waveform caused by blood flow to the two ocular globes through which impairment of the blood flow in one internal carotid artery relative to the other is indicative of extracranial carotid occlusive disease.

Specifically, apparatus comprising eye cups having an orifice therethrough adhering to the eye by vacuum means enable connective flexible tubing interior air channel access for pressure transducers to measure the ocular globe pulsations. The flexible tubing connecting the eye cup and transducer is additionally connected to a plurality of valves, vacuum pump, and regulator, whereby the regulator and the vacuum pump create a desired partial vacuum and, by means of valves, isolation of air channels between each ocular globe and respective transducer may be accomplished. Upon isolation of each air channel, each ocular pulse wave may be measured without interference in order that differential delays between pulse waves may be determined as indicative of possible stenosis or occlusion in the internal carotid arteries.

8 Claims, 5 Drawing Figures

APPARATUS FOR OCULAR PLETHYSMOGRAPHY

BACKGROUND OF THE INVENTION

This invention relates to apparatus for conducting ocular plethysmography (OPG) tests by noninvasive means.

The recognition of extracranial carotid occlusive disease as a major remediable cause of strokes in persons has resulted in increased research into means and methods whereby flow reducing lesions of the internal carotid artery may be detected. Potential stroke candidates create a need for effective noninvasive means to improve the selection of patients for surgical intervention.

The left and right common carotid arteries which are located on opposite sides of the neck and lower face, each bifurcate into the internal carotid artery running to the same sided eye and external carotid artery to the same sided ear. The internal carotid artery additionally supplies blood to the same side of the brain. It has been known that occlusive plaque may build up at this bifurcation, creating a stenosis which tends to reduce the passage of blood through the arteries. This reduced blood flow results in a delay of blood flow pulses sensed at the eye and ear. Delays between similarly situated points on pulsatile wave forms at each eye and each ear is indicative of this occlusive plaque buildup. Should there be equal occlusive plaque buildup in each internal carotid artery, ideally, similarly situated points on the waveform, i.e., crest or trough, at each eye would be the same. However, extracranial carotid occlusive disease of equal severity is relatively rare. Therefore, in most cases, in the presence of the disease, there will be unequal delays in similarly situated points upon the waveform pulsatile waves at the eyes indicative of varying degrees of severity of the disease.

There have been a number of papers written and inventions made in this field, such as for example, Oculoplethysmography; An Adjunct To Arteriography In The Diagnosis Of Extracranial Carotid Occlusive Disease, *American Journal of Surgery*, Vol. 132, December 1976, Kartchner, McRae, Crain, and Whitaker, and U.S. Pat. No. 3,911,903, William Gee, et al. The Patent of Gee describes method and apparatus for determining blood pressure pulse waves at the eye under varying vacuum conditions, but utilizes large amounts of apparatus together with extremely complicated means attempting to isolate one eye and its associated transducer from the other eye and its associated transducer, and never completely isolates different eye-transducer communication mediums.

SUMMARY OF THE INVENTION

The present invention comprises apparatus whereby blood pulsatile waves in each eye may be detected for the comparison of relative delays of the pulse waves reaching one eye relative to the other and both eyes compared to each ear. These delays may be analyzed to determine the buildup of occlusive plaque in the carotid artery. More specifically, Applicant's invention comprises apparatus consisting of eye cups having a central orifice therethrough and air pressure transducers, each eye cup and respective transducer interconnected by tubing of substantially equal length, and valve means, vacuum pump means, and partial vacuum regulator means connecting to a manifold which in turn connects to both flexible tubes interconnecting the eye cups to their respective transducer. By means of the plurality of valves, vacuum pump, and regulator, a desired partial vacuum is established in all connected tubing to assure proper adhesion of the eye to the annular periphery of the eye cup and equal pressure in each tube connecting the eye cup to the transducer. Thereafter, each tube is isolated from the other by means of the valve system and measurement of the blood pulse waveform is taken via the air channel by the transducer for delay time comparison. After the tests are completed, the partial vacuums created in each side are released allowing atmospheric air to enter the system and thereby facilitating removal of the eye cup.

Accordingly, it is an object of the present invention to provide apparatus for measuring blood pulsatile waves of the eye.

Another object of this invention is to provide apparatus for measuring blood pulse waves of each eye where the eye pulse wave measurements are isolated one from the other.

A further object of this invention is to provide apparatus for creating equal partial vacuums in two isolated eye blood pulse wave measurements.

DETAILED DESCRIPTION

The embodiment of this invention which detects for simultaneous measurement the arrival of bilateral ocular pulsations representing the volume change of each eye produced by the pulsatile arterial blood flow is as follows.

Figure 1:
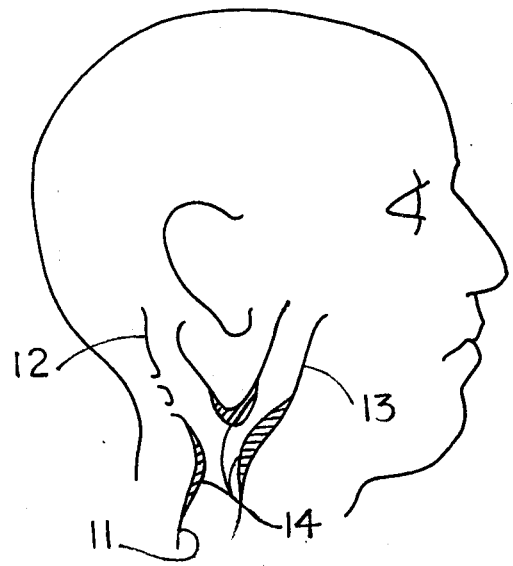
FIG. 1 is a side view of a person's head showing the occlusive buildup in the carotid artery.

Reference to FIG. 1 shows a simplified and idealized narrowing or stenosis primarily located in the right internal carotid artery 13 after it branches off from the right common carotid artery 11. As can be seen from FIG. 1, there is some stenosis of the right common carotid artery 11 and the right external carotid artery 12 which is directed to a person's ear. The right internal carotid artery 13 is directed to the right eye and to the brain. The occlusive plaque 14, or buildup of matter, at the bifurcation and entrance to the right internal carotid artery forming the stenosis causes delay in the arrival time of the blood pulse wave to the right eye. The left side of the face and neck (not shown) similarly contains the left common carotid artery bifurcating into its left internal carotid artery and left external carotid artery.

Since both right and left carotid arteries are initially supplied blood by the beating of the person's heart, the blood pulse wave produced by each beat of the heart may be detected at the ocular globe by volume fluctuations, the ocular globe generally reaching its maximum volume at systole and minimum volume at diastole, disregarding delays. Any differences in arrival time of the blood pulse waves at the eyes finds as one of its possible causes a stenosis at or near a common carotid artery bifurcation. Should both carotid arteries have equal stenosis, the pulse wave arrival time should be the same in both eyes, however, should there be stenosis on one carotid artery only, or unequal stenosis in both carotid arteries, the pulse wave arrival time will be unequal. As stated before, it is the discovery of the stenosis indicative of extracranial carotid occlusive disease that is sought.

Figure 2:
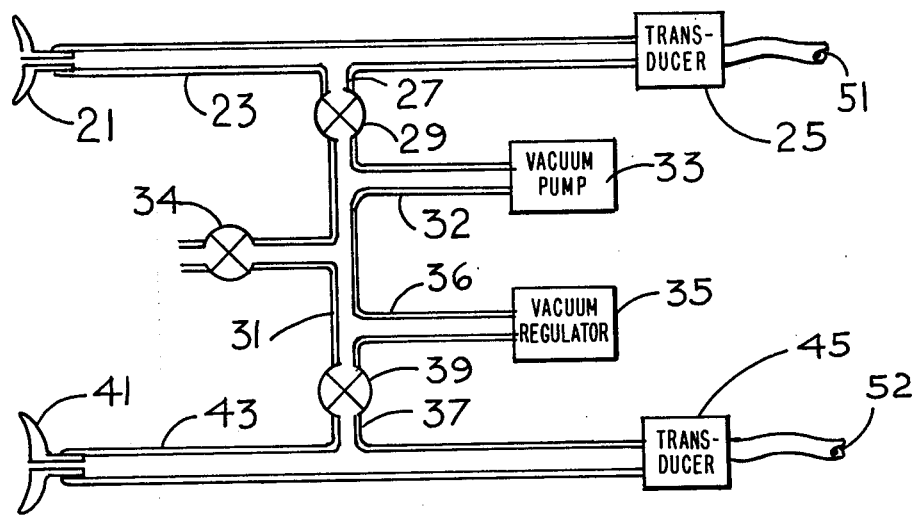
FIG. 2 is a block diagram of the inventive apparatus system.

Reference now to FIG. 2 shows the inventive apparatus by which the bilateral ocular pulsations are detected. Eye cup 21 having an orifice therethrough is placed upon the cornea or sclera of a patient's eye which may have been previously anesthetized as desired. Eye cup 21 has a hollow stem protruding from the cup's convex side communicating with an orifice through the eye cup, which stem is encompassed by one end of flexible tubing 23. Eye cup 21 is so constructed that its inner concave side is of a less radius than the radius of the ocular globe such that the ocular globe meets the peripheral surface or rim of the eye cup. Distal the eye cup and connecting with flexible tubing 23 is air pressure transducer 25 which communicates with the ocular globe (not shown) through the orifice and hollow stem of eye cup 21 and the air channel of tubing 23. Similarly constructed as eye cup 21, flexible tubing 23, and transducer 25, is eye cup 41, flexible tubing 43 and transducer 45 which is adapted to attach to the patient's other eye. It is noted that for best results, flexible tubing 23 and flexible tubing 43 should be the same length.

Interposed eye cup 21 and transducer 25, and connected to and communicative with the air channel of flexible tubing 23, is manifold 31. Manifold 31 is also interposed eye cup 41 and air pressure transducer 45 and connected to and communicative with the air channel of flexible tubing 43. At distal ends in manifold 31 are air valves 29 and 39, valve 29 permitting interruption of the air channel from flexible tube 23 through the end portion tube 27 of manifold 31. Similarly, air valve 39 permits alternate opening and closing the air channel between manifold 31 and flexible tube 43 through the end portion tube 37 of manifold 31.

Valves 29 and 39 are mechanically or electrically operated air valves which are in sealed relationship with distal portions 27 and 37 of manifold 31 to the air channel interior to manifold 31. Connecting with manifold 31 interposed valve 29 and valve 39 is air valve 34, vacuum pump 33, and vacuum regulator 35. Air valve 34 vents to the atmosphere the air channel interior to manifold 31. Manifold 31 may comprise many types of containers having the interior plenum, not excluding flexible tubing such as the type used in flexible tubes 23 and 43. Similarly, tubes 23 and 43 may comprise alternately flexible and semiflexible tubing, or, for that matter, flexible tubing attached to rigid metal or plastic tubing.

As can be seen in FIG. 2, all parts of the invention are interconnected by internal air channels which are in open communication when air valves 29 and 39 are open. Similarly, all air channels illustrated may be placed in air communication with the atmosphere when valve 34 is open.

Attached to and emanating from air pressure transducers 25 and 45 are electrical wire sets 51 and 52 respectively, which provide electrical communication to the recording and analyzing equipment (not shown) which record the detection of the arrival of the blood pulse waves in the ocular globes by their volumetric changes which in turn are reflected as air pressure changes in flexible tubing 23 and 43.

Figure 3:
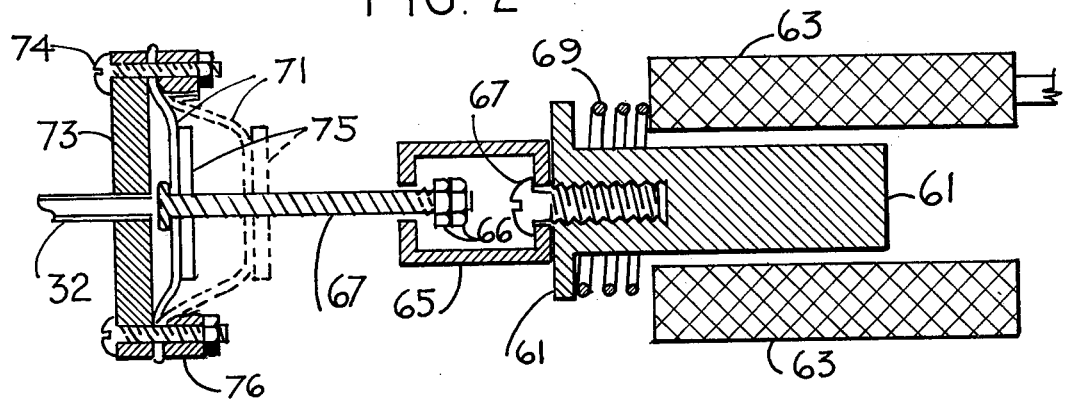
FIG. 3 is a cross-section view of the vacuum pump.

Reference now to FIG. 3, the construction of vacuum pump 33 is shown in cross-sectional detail. Shown in FIG. 3 is the solenoid plunger arrangement where plunger 61 partially nests interiorly to solenoid 63 with linkage 65 connecting to plunger 61 by screw means 67. A return spring 69 is provided between a lip on plunger 61 and the body of solenoid 63 whereby the plunger is returned to its resting position when the solenoid is not energized. Passing through an orifice in linkage 65 is pump arm 67 which in turn attaches to diaphragm 71 and diaphragm plate 75. Upon pump arm 67 internally to linkage 65 are screw nuts 66 providing means to adjust pump arm 67 travel for a constant travel by plunger 61 and linkage 65. Nuts 66, which are engaged by linkage 65 when plunger 61 retracts are adjusted according to the desired displacement of flexible diaphragm 71.

Flexible diaphragm 71 and diaphragm plate 75 which acts as a stiffener to diaphragm 71, is held in airtight configuration against flat plate 73 through which penetrates an air channel connecting with tubing 32. Normally an annular ring 76 and screw means 74 hold flexible diaphragm 71 in position. Diaphragm 71 may be constructed of soft rubber or stretchable plastic and has a greater part of its surface adhering to diaphragm plate 75, both of which attach to pump arm 67. Flat plate 73 may be constructed of plastic or metal as desired. Plunger 61 must be such material as to be attracted by electromagnetic field set up by coils of solenoid 63.

While a simple diaphragm construction has been shown in pump 33, the diaphragm construction obviously extends to other types of diaphragms, such as one where the diaphragm material would be folded over at the periphery of the diaphragm plate and rolls upon itself as the diaphragm is stretched.

Figure 4:
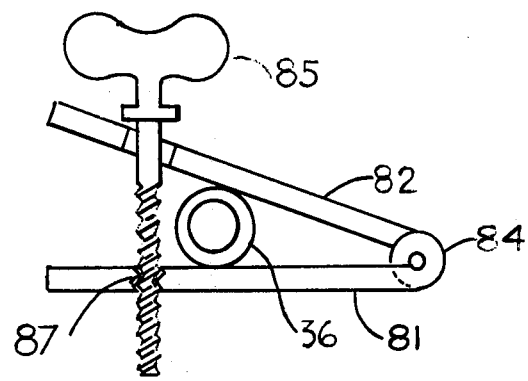
FIG. 4 is a cross-section view of the vacuum regulator.

FIG. 4 illustrates a simplified vacuum regulator of the plenum created within the manifold and tubing network as shown in FIG. 2. Tubing 36, which also is shown in FIG. 2 connecting into manifold 31, is held between arms 81 and 82 which pivot at hinge 84 with their central angle adjusted by thumb screw 85. Thumb screw 85 is held in place by an opening through arm 82 and machine threads in arm 81. Adjustment of thumb screw 85 will cause collapsing of flexible tubing 36 which decreases the volume of the air channel in tubing 36 and thereby adjusts the total volume of the plenum formed from the air channels of the invention.

Operation of the described apparatus to detect and measure pressure differentials at the eyes because of eye volume changes due to the blood pulse wave is as follows. Prior to placing the eye cups on the cornea or sclera of the patient's eyes, all air valves 29, 39, and 34 should be closed. Then vacuum pump 33 is energized by passing a current through solenoid 63 which in turn retracts plunger 61 into its central portion and thereby brings with it linkage 65. After linkage 65 has travelled a measured distance, it engages nuts 66 of pump arm 67 which, upon continued travel of plunger 61, extracts flexible diaphragm 71 creating a partial vacuum in the cavity formed by diaphragm 71 and flat plate 73. This partial vacuum, by means of tubing 32 extracts air from the interior of manifold 31 creating a partial vacuum throughout manifold 31 interior to the three air valves.

If it is desired that the pressure of the partial vacuum created within manifold 31 be changed at this point, such change may be made by means of regulator 35.

Prior to the engaging of pump 33, regulator 35 had been adjusted such that the volume interior to tubing 36 was nominally reduced to one-half. Of course, tubing 36 is sealed on its end distal to manifold 31 after it passes through regulator 35.

The patient is asked to lie down in a supine position with open eyes and eye cup 21 is placed upon the cornea or sclera of the eye. Valve 29 is then opened permitting air internal to flexible tube 23 to enter manifold 31, however, the partial vacuum is still maintained as the volume of the pump, diaphragm and manifold are substantially greater than the volume of the flexible tubing air channel. Air pressure then upon eye cup 21 and internal pressure to the ocular globe causes the eye to adhere to the peripheral surface or rim of eye cup 21 and the cornea or sclera is placed in communication with air pressure transducer 25 through the means of the air channel of tube 23. At this point, the same procedure is repeated with eye cup 41, placing eye cup 41 upon the patient's other eye and opening air valve 39. Now air pressure transducer 45 is in direct communication with the cornea or sclera of the other eye by means of air channel through flexible tube 43. At this point the same pressure exists through all air channels of the invention.

Again, at this time, regulator 35 may be utilized to fine tune the pressure existing within the partial vacuum of the tubing, to increase or decrease the partial vacuum as desired for optimum results.

Now, valves 29 and 39 are closed, vacuum pump 33 is de-energized and air valve 34 is open. This permits the interior of manifold 31 to return to atmospheric pressure and isolates the air channels of flexible tubes 23 and 43.

Now air pressure transducers 25 and 45 may measure their respective blood pulse waves as a function of volume change of the patient's eyes through the medium of the air channel internal to flexible tubes 23 and 43. Transducer outputs of the measurements are communicated to the analyzing and recording equipment (not shown) by means of electrical lead lines 51 and 52.

After the test is complete, the eye cups are removed from the eyes as follows. First, air valve 29 is opened allowing atmospheric air to enter the air channel of flexible tube 23 relieving the partial vacuum therein and releasing the air pressure upon and holding eye cup 21 to the eye and permitting its removal. Similarly, air valve 39 is opened allowing atmospheric air to enter the air channel of flexible tube 43 and similarly permitting eye cup 41 to be removed from the other eye.

It is noted that there are many variations within the state of the art by which parts within the invention may be constructed and it is intended that this invention not be limited to the specific construction which has been detailed. For example, vacuum pump 33 might comprise a piston cylinder arrangement or, for that matter, a large plenum already under a partial vacuum. Similarly, the diaphragm construction might comprise bellows or other similar air pump means. Additionally, regulator 35 may be means by which a volume is varied, such as a fixed diaphragm or adjustable piston cylinder arrangement. Also, as is obvious to one skilled in the art, regulator 35 may be placed in line between vacuum pump 33 and manifold 31 as it will accomplish the same purpose regardless of where it is located within the manifold, valve, and pump assembly.

As seen from FIGS. 2 through 4, the apparatus comprising this invention may be easily constructed or comprise devices commercially available. For example, the air pressure transducer is model BT-70 pressure transducer manufactured by the BioTec Instruments of Pasadena, Calif. The tubing may be polyethylene, rubber, vinyl, or any flexible small diameter tubing which has sufficient resiliency in its walls to withstand the slight partial vacuum created. The eye cups are commercially available devices that are well known in the medical field and have been utilized in the inventions and references already cited by Applicant. Additionally, air valves 29, 39, and 34 are commercially available valves of standard construction and the solenoid plunger arrangement is manufactured by Skinner, Model No. V-105.

Figure 5:
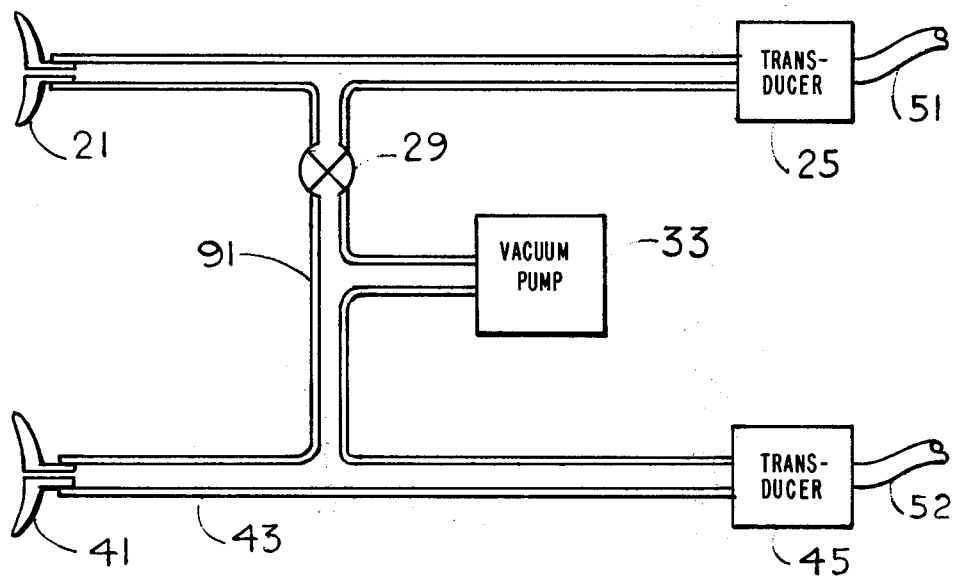
FIG. 5 is a block diagram of an alternate embodiment of the invention.

A still further embodiment of the invention is shown in FIG. 5 where air valves 34 and 39 together with regulator have been eliminated, there only remaining air valve 29 and vacuum pump 33, together with the respective eye cups and air pressure transducers.

The apparatus as shown in FIG. 5 operates slightly different than the description given above for the apparatus as shown in FIG. 2. In particular, utilizing apparatus of FIG. 5, prior to placing the eye cups 21 and 41 upon the patient's two eyes, air valve 29 is opened and vacuum pump 33 is in its rest state, i.e., no partial vacuum created. The patient is asked to lie supine, and eye cups 21 and 41 placed upon the cornea or sclera of the eyes. The eyes have previously been anesthetized if necessary. At this time, atmospheric pressure exists in the air channels of equal lengths of flexible tubing 43 and 23 as well as in the manifold tubing 91. After the eye cups 21 and 41 have been seated upon the patient's eyes, pump 33 is engaged creating the partial vacuum which extends through all air channels in all interconnecting tubing. At this point, the partial vacuum created within the air channel and within the under surface of the eye cups 21 and 41, permit atmospheric pressure to press the eye cups 21 and 41 upon the patient's eyes and urge the patient's ocular globes to adhere to the peripheral edge of the cup. Next, air valve 29 is closed, thus isolating air channel through flexible tubing 23 from the air channel through flexible tubing 43. Air pressure transducers 25 and 45 then may record their measurements, which, through the means of electrical leads sets 51 and 52 are directed to the measuring and recording apparatus (not shown).

It is noted that in the operation of the embodiment shown in FIG. 5 and the operation of the embodiment shown in FIG. 2, air pressure transducers 25 and 45 do not measure sound waves as such but measure the increase and decrease of the air pressure within the air channels of the connecting tubing which are changed by the change of the eye contour due to volume changes in the eye because of the blood pulse waves. These are very small volume changes and the air pressure transducers are very sensitive devices.

After the transducers 25 and 45 have made their measurements, air valve 29 is opened allowing the air channels through flexible tubing 23 and 43 to be in open communication with each other and vacuum pump 33 is permitted to go to its rest state. This permits the air within the air channels of all the tubing to return to atmospheric pressure and permits lifting of eye cups 21 and 41 from the patient's eyes.

It is noted that should measurements taken of the volume changes of one ocular globe appear erratic or otherwise unusual, the apparatus may be checked for air leaks or malfunctions by merely reversing the eye cups, eye for eye. If the erratic measurement follows the eye cup, air leaks in specific areas of the equipment and/or malfunctions of specific pieces of apparatus are suspect. This method of apparatus check may be easily implemented where the eye cups, flexible tubing, manifold, air valves, and regulator are packaged in one unit suspended above the person's face. Further if this unit is connected with an upright stand where the unit may be rotated by 180°, by means of said rotation the eye cups and attached flexible tubing may be easily reversed upon the patient's eye. This configuration and location of the equipment anticipates that the vacuum pump is located away from the manifold, connected by tubing. Because of the relatively small size of the pump, the above configuration need not, however, be necessary.

While a preferred embodiment and an alternate have been shown and described in detail, there are obviously many other embodiments and variations in configurations which can be made by a person skilled in the art without departing from the spirit, scope, or principle of this invention. Therefore this invention is not to be limited except in accordance with the scope of the appended claims.

I claim:

1. Apparatus for detecting ocular pulsations of a person's eyes produced by pulsatile arterial blood flow comprising first and second eye cup means, both said eye cup means having an air passageway therethrough; first and second air pressure transducer means; first and second air tube means operably connecting said first eye cup means to said first transducer means and said second eye cup means to said second transducer means respectively; vacuum pump means operably connected to said first air tube means and said second air tube means; and air valve means interposed said vacuum pump means and said first air tube means whereby when said eye cups are placed upon a person's eyes and a partial vacuum is created in the air tubes by the vacuum pump, the air pressure transducer means are placed in sealed air communication with the person's eyes and said air valve means may be closed to interrupt communication and interference between said first and second air tube means and thereby isolate said first and second air tube means from each other in order that ocular pulsations of each eye may be separately detected.

2. Apparatus for detecting ocular pulsations as defined in claim 1 wherein said vacuum pump means comprises magnetic solenoid-plunger means, said solenoid-plunger means including adjusting arm means, and diaphragm means, said diaphragm means including a flexible diaphragm and face plate attached to the periphery of said flexible diaphragm in air sealed relationship, said adjusting arm means connected to said diaphragm means whereby when said solenoid-plunger means is activated, said adjusting arm means deforms said flexible diaphragm creating a partial vacuum between said diaphragm and said face plate, creating the partial vacuum.

3. Apparatus for detecting ocular pulsations in a person's eyes produced by pulsatile arterial blood flow comprising a first and second eye cup means for attachment to a person's eyes, a first and second air pressure transducer means, a first and second tube means operably connecting said first eye cup and said first transducer and said second eye cup and said second transducer respectively, manifold means operably connecting said first tube means and said second tube means, vacuum pump means connected to said manifold means, and first valve means interposed said manifold means and said first tube means whereby both eye cup means, both transducer means, both tube means, and vacuum pump means are in air communication and said vacuum pump may create a partial vacuum in each eye cup means adhering the eye cups to the eyes and thereby providing a direct air channel between an associated eye and a transducer.

4. Apparatus for detecting ocular pulsations as defined in claim 3 further comprising air volume regulator means connecting with said manifold means whereby when said vacuum pump operates, said volume manifold varies the enclosed volume and thereby regulates the air pressure of said partial vacuum so created.

5. Apparatus for detecting ocular pulsations as defined in claim 4 wherein said volume regulator means comprises a first and second arm means, said first and second arm means operably attached at one end of each arm to form an angle, thumb screw means penetrating said first arm means other end and screwing into said second arm means other end, and third tube means interiorly the angle formed by the said first and second arm means, one end of said third tube means operably attached to said manifold and the other end of said third tube means closed off, whereby said thumb screw means may be screwed into screw receiving second arm means thereby reducing the volume interiorly to said third tube means.

6. Apparatus for detecting ocular pulsation as defined in claim 4 further comprising second valve means interposed said manifold means and said second tube means whereby after said vacuum pump means has established a partial vacuum in both said eye cup means and said tube means, both said first and second valve means may be closed and isolate said first tube means from said second tube means in order that said ocular pulsations from each eye will not interfere with each other.

7. Apparatus for detecting ocular pulsations as defined in claim 6 further comprising air volume regulator means connecting said manifold means whereby the air pressure created by said vacuum pump means may be regulated by varying the enclosed volume.

8. Apparatus for detecting ocular pulsations as defined in claim 6 further comprising third air valve means connecting said manifold means to the atmospheric air whereby the partial vacuum created within said manifold may be vented to the atmosphere after said ocular pulsations are detected in order to facilitate removal of the eye cups from the person's eyes by releasing the partial vacuum created therein.

* * * * *